US007335787B2

United States Patent
Tomita et al.

(10) Patent No.: US 7,335,787 B2
(45) Date of Patent: Feb. 26, 2008

(54) METHOD FOR PRODUCING ONIUM SALT DERIVATIVES, AND NOVEL ONIUM SALT DERIVATIVES

(75) Inventors: Kyoichi Tomita, Chiba (JP); Shinji Ishii, Chiba (JP)

(73) Assignee: Toyo Gosei Kogyo Co., Ltd., Ichikawa-shi, Chiba (JP)

( * ) Notice: Subject to any disclaimer, the term of this patent is extended or adjusted under 35 U.S.C. 154(b) by 668 days.

(21) Appl. No.: 10/660,255

(22) Filed: Sep. 11, 2003

(65) Prior Publication Data

US 2005/0176982 A1    Aug. 11, 2005

Related U.S. Application Data

(62) Division of application No. 09/890,842, filed on Aug. 3, 2001, now Pat. No. 6,620,957.

(30) Foreign Application Priority Data

| Dec. 3, 1999 | (JP) | ............................. 11-345488 |
| Mar. 9, 2000 | (JP) | ............................. 2000-065213 |
| Aug. 30, 2000 | (JP) | ............................. 2000-260928 |
| Sep. 19, 2000 | (JP) | ............................. 2000-284186 |
| Sep. 21, 2000 | (JP) | ............................. 2000-286306 |

(51) Int. Cl.
*C07C 305/00* (2006.01)
*C07C 303/32* (2006.01)

(52) U.S. Cl. ............................. 558/20; 558/36; 558/38; 558/58; 558/59

(58) Field of Classification Search ............... None
See application file for complete search history.

(56) References Cited

U.S. PATENT DOCUMENTS

| 2,201,814 A | 5/1940 | Evans et al. |
| 3,758,594 A | 9/1973 | Campen et al. |
| 3,996,147 A | 12/1976 | Settineri et al. |
| 4,045,549 A | 8/1977 | Gerecht |
| 4,056,634 A | 11/1977 | Della Bella et al. |
| 4,603,101 A | 7/1986 | Crivello |
| 4,981,881 A | 1/1991 | Crivello |
| 5,149,857 A | 9/1992 | Takeda et al. |
| 5,824,824 A | 10/1998 | Osawa et al. |
| 5,855,820 A | 1/1999 | Chan et al. |
| 6,620,957 B1 * | 9/2003 | Tomita et al. ............... 558/20 |

FOREIGN PATENT DOCUMENTS

| EP | 104143 | 9/1983 |
| EP | 115466 | 1/1984 |
| EP | 0334056 | 9/1989 |
| JP | 5998103 | 9/1983 |
| JP | 59141557 | 8/1984 |
| JP | 227660 | 6/1990 |
| JP | 3192173 | 8/1991 |
| JP | 1033364 | 10/1996 |
| JP | 10330353 | 5/1997 |
| JP | 1138623 | 9/1997 |
| JP | 107650 | 1/1998 |

OTHER PUBLICATIONS

Acetylenic Esters. Preparation and Characterization of Alkynyl Dialkyl Phosphates, RC=COPO(OR')$_2$, J.Am.Chem.Soc, 1989, pp. 2225-2230.
Synthesis and Properties of (Perfluoroalkyl) Phenyliodonium Triflates (Fits Reagents) and Their Analogues. Journal of Fluorine Chemistry, 31, 1986, pp. 37-56.
Snythesis and reactivity of benzylic sufonium salts: benzylation of phenol and thiophenol under newar-neutral conditions;Tetrahedron by Forrester et al., 2001, vol. 57 pp. 2871-2884.
Alkyldimethylsufonium methylsufonatesCA:87:200789 abs of JP52083330, Jul. 1977.

* cited by examiner

*Primary Examiner*—Yvonne Eyler
*Assistant Examiner*—Yevgeny Valenrod
(74) *Attorney, Agent, or Firm*—Brian A. Gomez; Gomez International Patent Office, LLC

(57) ABSTRACT

The invention provides a high-yield method for producing onium salt derivatives useful as agents, such as acid-generators, employed in chemically amplified resists; and to provide novel onium salt derivatives. Reaction of an onium salt derivative containing a halide anion or a carboxylate anion with a sulfonic acid ester derivative or a phosphoric acid derivative provides an onium sulfate derivative or an onium phosphate derivative at high yield.

3 Claims, No Drawings

METHOD FOR PRODUCING ONIUM SALT DERIVATIVES, AND NOVEL ONIUM SALT DERIVATIVES

CROSS-REFERENCE TO RELATED APPLICATION

This application is a Division of application Ser. No. 09/890,842, filed on Aug. 3, 2001 now U.S. Pat. No. 6,620,957.

TECHNICAL FIELD

The present invention relates to a method for producing an onium salt derivative useful as an onium-type strong-acid generator which generates a strong acid through irradiation with UV rays, a KrF excimer laser beam, an ArF excimer laser beam, an $F_2$ excimer laser beam, an electron beam, or an X-ray; and to a novel onium salt derivative.

BACKGROUND ART

In recent years, in conjunction with a trend of high-density mounting of semiconductor devices, the wavelength of a light source used in a light-exposure apparatus employed in photolithography—one of micro-processing method—has been shortened. Recently, application of a KrF excimer laser beam (248.4 nm) has been investigated. Thus, resist material to be irradiated with a KrF excimer laser beam serving as a light source is required to possess high sensitivity to the exposed light so as to cause reaction.

In connection with this, a method using chemically amplified resist material is proposed (*Polymn. Eng. Sci.*, Vol. 23, 1012 (1983)). According to the method, high sensitivity is attained by incorporating, into resist material, a compound which generates an acid through exposure to light.

Examples of the compound which generates an acid through exposure to light (hereinafter called an acid generator) and incorporated into the aforementioned chemically amplified resist material include onium salts such as diazoniumdiaryl salts, alkyliodoniumtriaryl salts, and alkylsulfonium salts, which are disclosed in a number of publications (e.g., in U.S. Pat. Nos. 4,491,628 and 4,603,101, Japanese Patent Publication (kokoku) No. 2-27660, and Japanese Patent Application Laid-Open (kokai) No. 62-1140).

Compounds such as 6-dinitrobenzyl tosylate are also disclosed as acid generators (e.g., F. I. Houliban et al., *Advances in Resist Technology and Processing, SPIE*, Vol. 920, 67, (1988)).

Among these acid generators, onium salts such as iodonium salts and sulfonium salts, inter alia, onium salt derivatives containing sulfonate as an anion, are widely used in view of their high stability of solution during storage.

There have been known methods for producing such onium salt derivatives, including salt exchange between an onium salt derivative containing a halide ion as an anion, and sulfonic acid, silver sulfonate, or alkali metal sulfonate (e.g., *J. Polymer Sci.*, Symposium No. 56, p. 383 (1976) and *J. Rad. Curing*, Vol. 4, p. 2 (1977)).

However, the above methods have drawbacks. Since exchange reaction between such an onium salt derivative and sulfonic acid or alkali metal sulfonate attains an equilibrium state, sulfonic acid or alkali metal sulfonate must be used in an amount of 1.5 mol-eq. or more based on the onium salt derivative containing a halide ion as an anion. In addition, migration of halide ions into the produced onium salt derivative containing sulfonate as an anion occurs. Furthermore, when a silver salt is used in the methods, cost for carrying out the reaction increases due to the high price of the silver salt.

Sulfonic acids which form these sulfonium salts serving as acid generators include a variety of species in terms of the substituent; from aromatic group to alkyl group. Therefore, it is preferable to obtain the sulfonic acids from a single common specific intermediate through anion exchange. However, since all sulfonic acids have an acidity stronger than that of sulfuric acid, sulfonate anions derived from the starting material unavoidably remain during a typical salt exchange process, due to equilibrium of the reaction, to thereby affect a resist containing the acid generators.

From another aspect, onium salt derivatives containing sulfonate as an anion are employed, for example, as thermal-polymerization or photo-polymerization initiators for a variety of anion-polymerizable compounds such as epoxy compounds and as photo-acid generators of chemically amplified resists.

In view of the foregoing, an object of the present invention is to provide a high-yield method for producing an onium salt derivative useful as an agent such as an acid generator used in chemically amplified resists. Another object of the invention is to provide a novel onium salt derivative.

The present inventors have carried out extensive studies in order to solve the aforementioned drawbacks, and have found that reacting an onium salt derivative containing a halide anion or a carboxylate anion with a sulfonic acid ester derivative or a phosphoric acid derivative can produce an onium sulfonate derivative or an onium phosphate derivative at high yield; that the reaction can provide a novel onium salt derivative containing phosphate as an anion; and that an onium salt derivative containing sulfonate as an anion can effectively be produced from the novel onium phosphate derivative. The present invention has been accomplished on the basis of these findings.

The present inventors have also found that a similar onium salt derivative containing sulfonate as an anion can be produced by reacting, in the presence of a specific compound such as an ortho acid ester, an onium salt derivative containing a halide anion or a carboxylate anion with a sulfonate salt. The present invention has been accomplished also on the basis of this finding.

Furthermore, the present inventors have also found that an onium sulfonate derivative can be produced at high yield by reacting an onium salt derivative containing a halide anion or a carboxylate anion with a sulfonic acid derivative such as dialkylsulfuric acid and, subsequently, with a sulfonate salt. The present invention has been accomplished also on the basis of this finding.

DISCLOSURE OF THE INVENTION

Accordingly, in a first mode of the present invention, there is provided a method for producing an onium salt derivative, characterized by comprising reacting an onium salt derivative represented by any one of formulas (1) through (4):

-continued

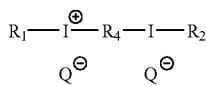 (2)

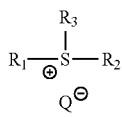 (3)

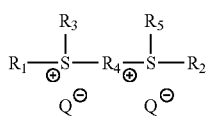 (4)

wherein each of $R_1$, $R_2$, $R_3$, and $R_5$ represents an alkyl group, a cycloalkyl group, a perfluoroalkyl group, an aromatic organic group, an aralkyl group, or a phenacyl group, each of these groups having $\leq 25$ carbon atoms and being optionally substituted; one or both of the pairs of $R_1$ and $R_3$, and $R_2$ and $R_5$ may together form a divalent organic group; $R_4$ represents a $C \leq 20$ divalent organic group; and Q represents a halide anion or a $C \leq 10$ carboxylate anion, with a compound represented by any one of formulas (5) through (7):

$R_6SO_2OR_7$ (5)

 (6)

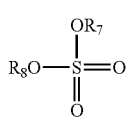 (7)

wherein $R_6$ represents an alkyl group, a cycloalkyl group, a perfluoroalkyl group, an aromatic organic group, or an aralkyl group, each of these groups having $\leq 25$ carbon atoms and being optionally substituted; $R_7$ represents an alkyl group, a cycloalkyl group, a perfluoroalkyl group, or an aralkyl group, each of these groups having $\leq 10$ carbon atoms and being optionally substituted; and each of $R_8$ and $R_9$ represents an alkyl group, a cycloalkyl group, a perfluoroalkyl group, or an aralkyl group, each of these groups having $\leq 10$ carbon atoms and being optionally substituted, to thereby yield an onium salt derivative represented by one of formulas (8) through (19).

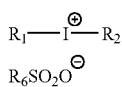 (8)

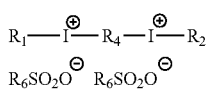 (9)

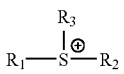 (10)

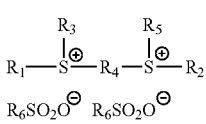 (11)

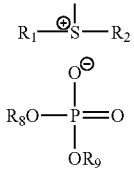 (12)

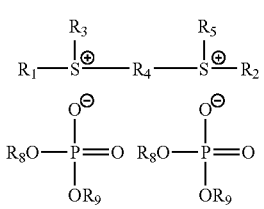 (13)

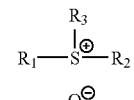 (14)

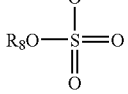 (15)

 (16)

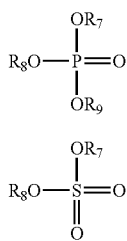 (17)

(18)

-continued

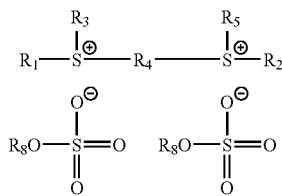
(19)

A second mode of the present invention is drawn to a specific mode of the first mode, and according to the second mode, there is provided a method for producing an onium salt derivative, wherein the sulfonic acid ester represented by formula (5) is a lower alkyl sulfonate in which $R_7$ is a lower alkyl group having 5 or fewer carbon atoms.

A third mode of the present invention is drawn to a specific mode of the first or the second mode, and according to the third mode, there is provided a method for producing an onium salt derivative, wherein reaction is carried out while removing generated $R_7Q$ from the reaction system.

A fourth mode of the present invention is drawn to a specific mode of any one of the first through third modes, and according to the fourth mode, there is provided a method for producing an onium salt derivative, wherein the reaction is carried out in a solvent.

In a fifth mode of the present invention, there is provided a method for producing an onium salt derivative, characterized by comprising reacting an onium salt derivative represented by any one of formulas (1) through (4):

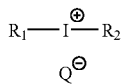
(1)

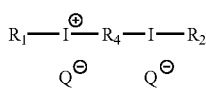
(2)

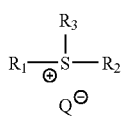
(3)

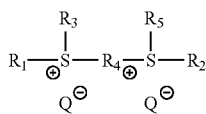
(4)

wherein each of $R_1$, $R_2$, $R_3$, and $R_5$ represents an alkyl group, a cycloalkyl group, a perfluoroalkyl group, an aromatic organic group, an aralkyl group, or a phenacyl group, each of these groups having ≦25 carbon atoms and being optionally substituted; one or both of the pairs of $R_1$ and $R_3$, and $R_2$ and $R_5$ may together form a divalent organic group; $R_4$ represents a C≦20 divalent organic group; and Q represents a halide anion or a C≦10 carboxylate anion, with a compound represented by any one of formulas (21) through (23):

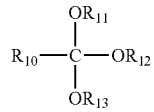
(21)

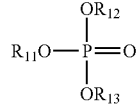
(22)

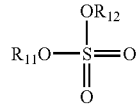
(23)

wherein $R_{10}$ represents hydrogen or an alkyl group, a cycloalkyl group, a perfluoroalkyl group, an aromatic organic group, or an aralkyl group, each of these groups having ≦25 carbon atoms and being optionally substituted; and each of $R_{11}$, $R_{12}$, and $R_{13}$ represents an alkyl group, a cycloalkyl group, a perfluoroalkyl group, or an aralkyl group, each of these groups having ≦10 carbon atoms and being optionally substituted;

and with a sulfonic acid derivative represented by formula (24):

$$R_{15}SO_2OY \qquad (24)$$

wherein $R_{15}$ represents an alkyl group, a cycloalkyl group, a perfluoroalkyl group, an aromatic organic group, or an aralkyl group, each of these groups having ≦25 carbon atoms and being optionally substituted; and Y represents a hydrogen atom, an alkali metal, or ammonium, to thereby yield an onium salt derivative represented by one of formulas (25) through (28).

(25)

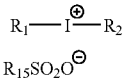
(26)

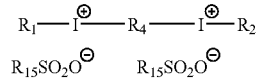
(27)

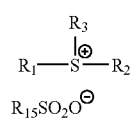
(28)

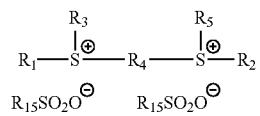

A sixth mode of the present invention is drawn to a specific mode of the fifth mode, and according to the sixth mode, there is provided a method for producing an onium salt derivative, wherein the compound represented by any one of formulas (21) through (23) is used in an amount by mol one to ten times that of the onium salt derivative represented by any one of formulas (1) through (4).

A seventh mode of the present invention is drawn to a specific mode of the fifth or the sixth mode, and according to the seventh mode, there is provided a method for producing an onium salt derivative, wherein the sulfonic acid derivative is used in an amount by mol one to two times that of the onium salt derivative represented by any one of formulas (1) through (4).

In an eighth mode of the present invention, there is provided a method for producing an onium salt derivative, characterized by comprising reacting an onium salt derivative represented by any one of formulas (1) through (4):

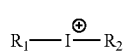

(1)

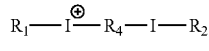

(2)

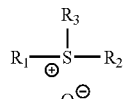

(3)

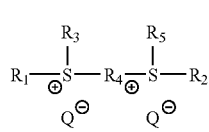

(4)

wherein each of $R_1$, $R_2$, $R_3$, and $R_5$ represents an alkyl group, a cycloalkyl group, a perfluoroalkyl group, an aromatic organic group, an aralkyl group, or a phenacyl group, each of these groups having $\leq 25$ carbon atoms and being optionally substituted; one or both of the pairs of $R_1$ and $R_3$, and $R_2$ and $R_5$ may together form a divalent organic group; $R_4$ represents a $C \leq 20$ divalent organic group; and Q represents a halide anion or a $C \leq 10$ carboxylate anion, with a sulfuric acid ester represented by formula (29):

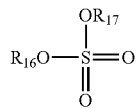

(29)

wherein each of $R_{16}$ and $R_{17}$ represents an alkyl group, a cycloalkyl group, a perfluoroalkyl group, or an aralkyl group, each of these groups having $\leq 10$ carbon atoms and being optionally substituted, to thereby form an onium salt derivative, and reacting the resultant onium salt derivative with a sulfonic acid derivative represented by formula (24):

 (24)

wherein $R_{15}$ represents an alkyl group, a cycloalkyl group, a perfluoroalkyl group, an aromatic organic group, or an aralkyl group, each of these groups having $\leq 25$ carbon atoms and being optionally substituted; and Y represents a hydrogen atom, an alkali metal, or ammonium, to thereby yield an onium salt derivative represented by one of formulas (25) through (28).

(25)

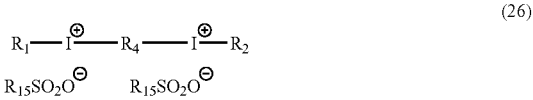

(26)

(27)

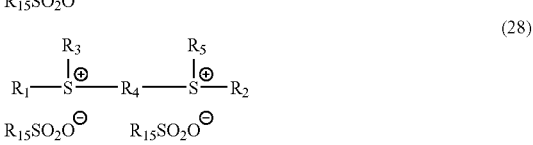

(28)

A ninth mode of the present invention is drawn to a specific mode of the eighth mode, and according to the ninth mode, there is provided a method for producing an onium salt derivative, wherein the sulfuric acid ester represented by formula (29) is dimethylsulfuric acid or diethylsulfuric acid.

In a tenth mode of the present invention, there is provided a method for producing an onium salt derivative, characterized by comprising reacting an onium salt derivative represented by any one of formulas (12) through (15):

(12)

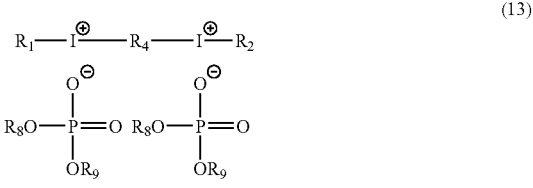

(13)

(14)

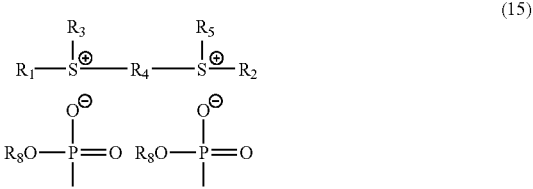

(15)

wherein each of $R_1$, $R_2$, $R_3$, and $R_5$ represents an alkyl group, a cycloalkyl group, a perfluoroalkyl group, an aromatic organic group, an aralkyl group, or a phenacyl group, each of these groups having $\leq 25$ carbon atoms and being optionally substituted; one or both of the pairs of $R_1$ and $R_3$, and $R_2$ and $R_5$ may together form a divalent organic group; $R_4$ represents a C≦20 divalent organic group; and each of $R_8$ and $R_9$ represents an alkyl group, a cycloalkyl group, a perfluoroalkyl group, or an aralkyl group, each of these groups having ≦10 carbon atoms and being optionally substituted, with a sulfonic acid derivative represented by formula (24):

$$R_{15}SO_2OY \qquad (24)$$

wherein $R_{15}$ represents an alkyl group, a cycloalkyl group, a perfluoroalkyl group, an aromatic organic group, or an aralkyl group, each of these groups having ≦25 carbon atoms and being optionally substituted; and Y represents a hydrogen atom, an alkali metal, or ammonium, to thereby yield an onium salt derivative represented by one of formulas (25) through (28).

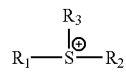
(25)

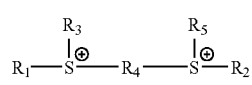
(26)

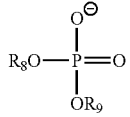
(27)

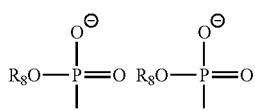
(28)

In an eleventh mode of the invention, there is provided a novel onium compound represented by any one of formulas (12) through (15):

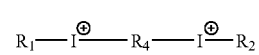
(12)

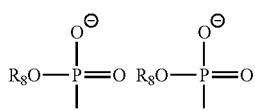
(13)

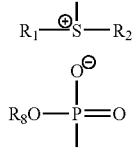
(14)

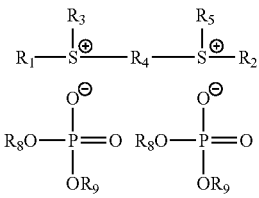
(15)

wherein each of $R_1$, $R_2$, $R_3$, and $R_5$ represents an alkyl group, a cycloalkyl group, a perfluoroalkyl group, an aromatic organic group, an aralkyl group, or a phenacyl group, each of these groups having ≦25 carbon atoms and being optionally substituted; one or both of the pairs of $R_1$ and $R_3$, and $R_2$ and $R_5$ may together form a divalent organic group; $R_4$ represents a C≦20 divalent organic group; and each of $R_8$ and $R_9$ represents an alkyl group, a cycloalkyl group, a perfluoroalkyl group, or an aralkyl group, each of these groups having ≦10 carbon atoms and being optionally substituted.

In the present invention, an onium salt derivative represented by any one of the aforementioned formulas (1) through (4), serving as a raw material, is reacted with an sulfonic acid ester, a phosphoric acid ester, or a sulfuric acid ester, to thereby produce an onium salt sulfonate derivative or an onium salt phosphate derivative at high yield.

Although the onium salt derivatives represented by formulas (1) through (4), serving as raw materials, include iodonium salts having a center element of iodine and sulfonium salts having a center element of sulfur, other onium salts, such as ammonium salts and phosphonium salts, may also be used.

Each of $R_1$, $R_2$, $R_3$, and $R_5$ represents an alkyl group, a cycloalkyl group, a perfluoroalkyl group, an aromatic organic group, an aralkyl group, or a phenacyl group, each of these groups having ≦25 carbon atoms and being optionally substituted; and one or, both of the pairs of $R_1$ and $R_3$, and $R_2$ and $R_5$ may together form a divalent organic group. Specific examples of these substituents will be described hereinbelow.

Examples of the alkyl group include C3-C8 linear, branched, or cyclic alkyl groups. Specific examples include a methyl group, an ethyl group, a propyl group, an iso-butyl group, a sec-butyl group, a tert-butyl group, an iso-amyl group, a sec-amyl group, a 2-methylbutyl group, a 2-methyl-2-butyl group, a 1,1-dimethylbutyl group, 2-hexyl group, a 1,1,1-trimethylbenzyl group, a 1,1-dimethylhexyl group, a cyclopropyl group, a cyclopentyl group, a cyclohexyl group, a cycloheptyl group, and a cyclooctyl group. Specific examples of the cycloalkyl group include C3-C20 cycloalkyl groups such as a cyclopropyl group, a cyclopentyl group, a cyclohexyl group, and a bicycloheptyl group, and specific examples of the perfluoroalkyl group include a trifluoromethyl group, a perfluoropropyl group, a perfluorobutyl group, and a perfluorooctyl group.

Examples of the aromatic organic group include organic groups having a mono-ring or condensed ring carbon ring structure or having an aromatic nucleus of a mono-ring or condensed ring. Examples of the aromatic nucleus in the aromatic organic group include a phenyl group, a biphenyl group, a naphthyl group, an anthryl group, and a phenanthryl group. These aromatic nuclei may have a substituent at an appropriate position. Examples of the substituent include C1-C12 alkyl groups (e.g., methyl, ethyl, propyl, butyl, and hexyl); C1-C12 alkoxy groups (e.g., methoxy, ethoxy, propoxy, and butoxy); C2-C11 acyl groups (e.g., acetyl and benzoyl); C2-C11 acyloxy groups (e.g., acetyloxy and benzoyloxy); C7-C20 aralkyl groups (e.g., benzyl, diphenylmethyl, and phenylpropyl); a nitro group; a cyano group; a butoxycarbonyloxy group; and halogen atoms (e.g., fluorine, chlorine, bromine, and iodine). The aromatic nuclei may have two or more different substituents.

Specific examples include aryl groups such as a phenyl group, a halogenated phenyl group, a hydroxyphenyl group, an alkoxyphenyl group, an aminophenyl group, an alkoxycarbonylphenyl group, a formylphenyl group, a thiophenyl group, a thioalkoxyphenyl group, and a cyanophenyl group.

Examples of the aralky group include C7-C20 aralkyl groups (e.g., benzyl, naphthylmethyl, anthranylmethyl, and diphenylmethyl). These aralkyl groups may have a substituent at an appropriate position of the aromatic nucleus, and examples of the substituent include those described in relation to the aforementioned aromatic organic group.

Specific examples include a phenylbenzyl group, a halogenated benzyl group, a hydroxybenzyl group, an alkoxyphenylbenzyl group, an aminobenzyl group, an alkoxycarbonylbenzyl group, a formylphenyl group, a thiobenzyl group, a thioalkoxybenzyl group, and a cyanobenzyl group.

Examples of $R_4$ include divalent organic groups such as an arylene group, an alkylene group, a cycloalkylene group, and an aralkylene group. Specific examples include a phenylene group, a naphthylene group, an ethylene group, a propylene group, a butylene group, a hexylene group, a cyclohexylene group, and a xylylene group.

The divalent organic group which is formed by joining one or both of the pairs of $R_1$ and $R_3$, and $R_2$ and $R_5$ in formulas (3) and (4) is a divalent organic group which forms, in combination with a sulfur atom in the compound represented by formula (3) or (4), an aliphatic or an aromatic heterocyclic structure. Examples of such divalent organic groups include organic groups represented by the following formulas.

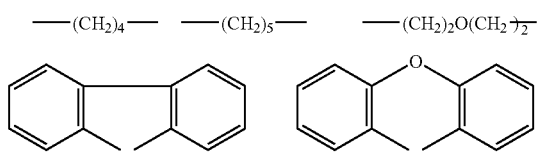

Q represents a halide anion or a C≦10 carboxylate anion.

Examples of the halide anion include a fluoride ion, a chloride ion, a bromide ion, and an iodide ion.

The carboxylate anion is selected from the group represented by the following formula (20):

$R_{19}$—COO (20)

wherein $R_{19}$ represents hydrogen or an alkyl group which has 10 or fewer carbon atoms and being optionally substituted. An alkyl group having 5 or fewer carbon atoms is preferred.

Compounds represented by formulas (5) through (7) which are to be reacted with an onium salt derivative represented by any one of formulas (1) through (4) are sulfonate esters, phosphate esters, and sulfate esters, respectively.

Specific examples of $R_6$ through $R_9$ are provided hereinbelow.

$R_6$ represents an alkyl group, a cycloalkyl group, a perfluoroalkyl group, an aromatic organic group, or an aralkyl group; each of which is optionally substituted and has 25 or fewer carbon atoms. Specific examples of $R_6$ are provided hereinbelow.

Examples of the alkyl group include optionally substituted C1-C20 alkyl groups such as methyl, ethyl, propyl, butyl, and hexyl.

Examples of the perfluoroalkyl group include trifluoromethyl, nonafluorobutyl, and perfluorooctyl.

Examples of the cycloalkyl group include C3-C15 cycloalkyl groups such as cyclopropyl, cyclopentyl, cyclohexyl, bicycloheptyl, and 7,7-dimethyl-2-oxo-bicyclo[2,2,1]heptane-1-methyl.

Examples of the aromatic organic group include C6-C25 aromatic organic groups such as phenyl, tolyl, trimethylphenyl, isopropylphenyl, triisopropylphenyl, t-butylphenyl, fluorophenyl, bis(trifluoromethyl)phenyl, difluorophenyl, trifluorophenyl, trifluoromethylphenyl, pentafluorophenyl, naphtyl, anthryl, 9,10-dimethoxyanthryl, and phenanthryl.

Examples of the aralkyl group include C7-C20 aralkyl groups such as benzyl, naphtylmethyl, anthranylmethyl, and diphenylmethyl.

Each of $R_7$, $R_8$, and $R_9$ represents an alkyl, a cycloalkyl, a perfluoroalkyl, or an aralkyl group; each of which is optionally substituted and has 10 or fewer carbon atoms. An alkyl group having 5 or fewer carbon atoms is particularly preferred.

Although the reaction of the present invention can be carried out in the presence or absence of a solvent, the reaction is preferably carried out in the presence of a solvent. Examples of the solvent to be used include halogenated hydrocarbons such as dichloromethane, chloroform, carbon tetrachloride, and chlorobenzene; ethers such as diethyl ether, diisopropyl ether, methyl t-butyl ether, and di-t-butyl ether; and nitriles such as acetonitrile and benzonitrile, with ethers being preferred.

No particular limitation is imposed on the reaction temperature of the present invention, and a range of 0° C.-200° C. is preferred.

The reaction of the present invention is transesterification, and compounds represented by $R_7$-Q (e.g., alkyl halides) are formed. Preferably, $R_7$-Q is removed from the reaction system. Thus, the lower the boiling point of $R_7$-Q, the easier the removal thereof. In an example method of removing $R_7$-Q formed through the reaction, a solvent having a boiling point higher than that of $R_7$-Q is employed and the reaction is carried out at a temperature higher than the boiling point of $R_7$-Q for vaporization and removal of $R_7$-Q.

The onium salt derivatives represented by formulas (8) through (19) produced through the above-described method can be used, without additional treatment, as agents such as acid generators. Alternatively, in accordance with needs, the onium salt derivatives may be used after being subjected to salt exchange reaction through a customary method. In particular, the onium salt sulfonate derivatives of formulas (16) and (17) are useful as onium-type strong-acid generators; which generate strong acid particularly through irradiation with UV rays, KrF excimer laser beams, ArF excimer laser beams, $F_2$ excimer laser beams, electron beams, or X-rays.

The onium salt phosphate derivatives represented by formulas (12) through (15) are novel compounds. They are onium having, as a counter ion to the onium moiety, a conjugated base of a weak acid (i.e., phosphate ester) as an anion moiety. Such an onium salt per se may be used as an acid generator. However, since such an onium salt readily undergoes salt exchange reaction with a strong acid such as sulfonic acid, there can be obtained an onium salt derivative having, as a counter ion to the onium moiety, a conjugated base of sulfonic acid, in a form free of impurities such as halogens.

When the onium salt phosphate derivative is produced by the aforementioned method of the present invention, the reaction may be carried out under the aforementioned reaction conditions. However, particularly suitable reaction conditions are provided hereinbelow.

A suitable amount of a phosphate ester for synthesis of the onium salt phosphate derivative is within a range of 1-3 equivalents, preferably 1.2-2 equivalents, based on 1 equivalent of a starting onium salt. In a case where the phosphate ester is employed as a solvent, a suitable amount of the phosphate ester is a range of 5-30 equivalents, more preferably 10-20 equivalents, based on 1 equivalent of the starting onium salt.

A suitable amount of a reaction solvent is within a range of 1-20 liters (hereinafter represented by "L"), preferably 5-10 L, based on 1 equivalent of the starting onium salt. Typically, a phosphate ester represented by formula (6) is employed as a reaction solvent. In other words, the phosphate ester represented by formula (6) serves not only as a reaction reagent but also as a reaction solvent. When the reaction of the present invention is carried out in the presence of a solvent, the species of the solvent is not particularly limited. Solvents such as a hydrocarbon solvent, a chlorine-containing solvent, an alcohol solvent, an ether solvent, a nitrile solvent, and an ester solvent may be used appropriately. Solvents of higher boiling point, such as 1,2-dichloroethane and dioxane, are preferred.

The reaction temperature typically falls within a range of 40-200° C., preferably 50-180° C. Unnecessarily higher temperature may cause a side reaction, resulting in a lower yield of the target compound. In contrast, lower reaction temperature prolongs the reaction time.

The reaction time typically falls within a range of 1 minute to 40 hours, preferably 5 minutes to 20 hours. Although the staring onium salts are insoluble at an initial period of the reaction, they dissolve as the reaction proceeds. However, diphenyliodonium chloride has very low solubility in solvents. In the case where a phosphate ester is used, upon cooling of the reaction mixture after completion of reaction, an onium salt crystallizes out. The crystallized onium salt is washed with a small amount of a solvent, such as alcohol, ether, or acetone, and then dried. The resultant compound may be used without any additional treatment when the compound is to be used for salt exchange reaction.

Although most onium phosphates are soluble in water, onium sulfonate salts formed through salt exchange reaction are taken up in an organic layer through extraction. In addition to equilibrium shift due to strong acidity, the sulfonate salts can be produced with nearly complete selectivity. The aforementioned production method of an onium phosphate utilizes the following reaction; i.e., a trialkyl phosphate undergoes nucleophilic substitution reaction, in which a halide serving as a nucleophilic agent reacts with an alkyl group of the trialkylphosphate, resulting in formation of a haloalkane, which is removed from the reaction system, thus facilitating the anion exchange. Thus, the production method is very effective.

Furthermore, when the above-described onium salt phosphate derivative serving as a starting material is reacted with the sulfonate salt represented by formula (24), the required amount of sulfonic acid can be reduced, and the yield of the target onium sulfonate derivative can be improved.

According to the method of the present invention, an onium dialkylphosphate is particularly preferred as the starting material. Salt exchange reaction thereof with a sulfonic acid forms an alkylphosphoric acid, which exhibits, in an aqueous solution, pKa of approximately 2. Since sulfonic acid exhibits a pKa of −3 to −6, which is greatly different from 2, the equilibrium shifts substantially toward the onium sulfonate salt.

In the method of the present invention, sulfonic acid is used in an amount of 1-2 mol, preferably 1.05-1.2 mol, based on 1 mol of the onium phosphate. The reaction solvent is used in an amount of 1-20 L, preferably 5-10 L, based on 1 mol of the onium salt.

In general, a halogen-containing solvent (e.g., methylene chloride or chloroform) is employed as a reaction solvent. However, any solvent may be used so long as it can form a separate layer from an aqueous layer and can dissolve an onium salt as a solute.

The reaction temperature is typically room temperature. The reaction time is not particularly limited, since the exchange reaction occurs instantaneously.

After completion of the reaction, the reaction mixture is alkalinized by adding water and an aqueous alkaline solution (e.g., an aqueous solution containing an amine such as ammonia), to thereby facilitate the exchange reaction and to facilitate the transfer of remaining acid to the aqueous layer. After removal of the aqueous layer, the organic layer is washed with water several times until pH is lower to a neutral region. The thus-obtained mixture is dried; the solvent is removed through distillation, and the residue is purified by treatment such as recrystallization, to thereby obtain a target compound.

Phosphate salts have a considerably low acidity as compared with a typical sulfonic acid and are usually water-soluble. In contrast, onium sulfonates formed via salt exchange are taken up into an organic layer through extraction. Thus, according to the method of the present invention, the acid equilibrium shifts toward the sulfonate salt, enabling production of a target compound in the form of sulfonate salt at nearly perfect selectivity.

According to the present invention, an onium salt derivative represented by any one of formulas (1) through (4), a compound represented by any one of formulas (21) through (23), and a sulfonate salt represented by formula (24) are cause to react in one step, to thereby produce an onium sulfonate salt at high yield.

The compounds represented by formulas (21) through (23) are orthocarboxylate esters, phosphate esters, and sulfate esters, respectively. $R_{10}$ in formula (21) is a hydrogen atom, or has the same meaning as the aforementioned substituent group $R_6$. Each of $R_{11}$ to $R_{13}$ of the compounds represented by formulas (21) through (23) has the same meaning as the aforementioned substituent groups $R_7$ and $R_8$.

$R_{15}$ of the sulfonate salt represented by formula (24) is an alkyl group, a cycloalkyl group, a perfluoroalkyl group, an aromatic organic group, or an aralkyl group; each having 25 or fewer carbon atoms and being optionally substituted. Specific examples of $R_{15}$ are provided hereinbelow.

Examples of the alkyl group include optionally substituted C1-C20 alkyl groups such as methyl, ethyl, propyl, butyl, and hexyl.

Examples of the perfluoroalkyl group include trifluoromethyl, nonafluorobutyl, and perfluorooctyl.

Examples of the cycloalkyl group include C3-C15 cycloalkyl groups such as cyclopropyl, cyclopentyl, cyclohexyl, bicycloheptyl, and 7,7-dimethyl-2-oxo-bicyclo[2,2,1]heptane-1-methyl.

Examples of the aromatic organic group include C6-C25 aromatic organic groups such as phenyl, tolyl, trifluoromethylphenyl, pentafluorophenyl, naphtyl, anthryl, 9,10-dimethoxyanthryl, and phenanthryl. Examples of the aralkyl group include C7-C20 aralkyl groups such as benzyl, naphtylmethyl, anthranylmethyl, and diphenylmethyl.

In formula (24), Y represents a hydrogen atom; an alkali metal such as lithium, sodium, or potassium; and/or ammonium. The group "ammonium" herein is represented by formula (31):

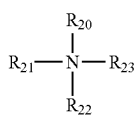

(31)

wherein each of $R_{20}$ to $R_{23}$ represents hydrogen, an alkyl group, an aralkyl group, or an aryl group.

The reaction involving such compounds and sulfonate salts is presumed to smoothly proceed via the following steps the aforementioned sulfonate compound is decomposed by acid catalytic action of sulfonic acid, to thereby yield cations. The formed cations are reacted with anions such as halide anions, to thereby form compounds such as alkyl halides. Thus, anions such as halide anions are removed, and, in turn, the sulfonic acid undergoes salt exchange reaction.

According to the above-described method of the present invention, a compound such as an ortho acid ester is used in an amount by mol of 1-10 times, preferably 1.2-5 times, that of the onium salt derivative.

The sulfonate salt is used in an amount by mol of 1-2 times, preferably 1.05-1.2 times, that of the onium salt derivative.

An appropriate solvent is employed in the reaction, and examples thereof include a chlorine-containing solvent, an alcohol solvent, an ether solvent, a nitrile solvent, an ester solvent, and a carboxylic acid solvent. Of these, methylene chloride and chloroform are particularly preferred.

Although the reaction generally proceeds at room temperature, the reaction can be accelerated by heating. Typically, the reaction temperature is not greater than 100° C., and preferably falls within a range of 40-60° C.

The reaction time depends on the reaction temperature. Reducing the anion concentration such as a halide anion concentration to not greater than 50 ppm requires 12 hours (at room temperature), or 2-4 hours (at 40° C.).

After completion of the reaction, the reaction mixture is alkalinized by adding aqueous ammonia. Subsequently, the target compound is taken up from the reaction solvent used through extraction. The thus-obtained solution is dried, the solvent is removed through evaporation, and the residue is recrystallized.

The above-described method of the present invention can provide onium sulfonates containing halides, which are detrimental to resist processes, at extremely low concentrations. Therefore, the onium sulfonates are useful as acid generators for chemically amplified resists.

Alternatively, according to the present invention, an onium salt derivative represented by any one of formulas (1) through (4) is reacted with a sulfate ester represented by formula (29), followed by reaction with a sulfonate ester represented by (24), to thereby yield an onium salt derivative having, as a counter ion to the onium moiety, a conjugated base of sulfonic acid. Such a method provides the target onium salt derivative of high purity in a simple, cost-effective manner.

The substituents $R_{16}$ and $R_{17}$ of formula (29) have the same meanings as $R_7$ and $R_8$ of formula (7). However, each of $R_{16}$ and $R_{17}$ is preferably an alkyl group having 5 or fewer carbon atoms, most preferably a methyl group and an ethyl group.

The above-described method of the present invention includes a first step comprising reaction of an onium salt derivative represented by any one of formulas (1) through (4) (hereinafter, description is provided on the assumption that the onium salt derivative contains a halogen serving as an anion), serving as a starting material, with a sulfate ester such as dialkylsulfuric acid (hereinafter, description is provided on the assumption that the sulfate ester is an alkyl ester). The first step yields an onium salt derivative having a monoalkylsulfate ion serving as a counterion.

This step is presumed to proceed in the following manner in which a halide-anion-containing onium salt derivative is reacted with a dialkylsulfuric acid, to thereby yield an alkyl halide and an onium salt derivative containing a monoalkylsulfate ion serving as a counter ion. Thus, halide anions can be removed from the reaction system by removing the alkyl halide formed through the reaction. The dialkyl sulfuric acid preferably has lower alkyl groups, with dimethyl sulfuric acid and/or diethyl sulfuric acid being particularly preferred. When a dialkyl sulfuric acid having lower alkyl groups is employed, the resultant substances, such as alkyl halide, can be vaporized and readily removed from the reaction system.

Although the first step may be carried out in the presence or absence of a solvent, this step is preferably carried out in the presence of a solvent. Examples of the solvent to be used include halogenated hydrocarbons such as dichloromethane, chloroform, carbon tetrachloride, and chlorobenzene; ethers such as diethyl ether, diisopropyl ether, methyl t-butyl ether, and di-t-butyl ether; and nitriles such as acetonitrile and benzonitrile. No particular limitation is imposed on the reaction temperature, and a range of 30-120° C. is preferred, with 40-100° C. being particularly preferred.

When an onium salt derivative having a halide anion as an anion moiety is reacted with a dialkylsulfuric acid, no particular limitation is imposed on the mol ratio of the onium salt derivative having a halide anion as an anion moiety to the dialkylsulfuric acid. However, a mol ratio within a range of 1.0:1.0-2.0 is preferred. When the mol ratio of the dialkylsulfuric acid is lower than 1.0:1.0, halide anions disadvantageously remain after completion of the reaction. The dialkylsulfuric acid may be used in a mol ratio of 2.0 or more. However, the greater the amount of employed dialkylsulfuric acid, the greater the amount of unreacted dialkylsulfuric acid.

In a second step, the onium salt derivative prepared in the first step and having, as a counter ion to the onium moiety, a conjugated base of a monoalkylsulfuric acid is reacted with a sulfonic acid and/or an alkali metal salt thereof and/or an ammonium salt thereof, to thereby yield a target onium salt derivative having, as a counter ion to the onium moiety, a conjugated base of a sulfonic acid. The sulfonic acid and salts thereof employed in the second step are represented by the aforementioned formula (24).

When the onium salt derivative having, as a counter ion to the onium moiety, a conjugated base of a monoalkylsulfuric acid is reacted with a sulfonic acid and/or a salt thereof in the second step of the present invention, no particular limitation is imposed on the mol ratio of the onium salt derivative having, as a counter ion to the onium moiety, a conjugated base of a monoalkylsulfuric acid to the sulfonic acid and/or a salt thereof. However, a mol ratio within a range of 1.0:1.0-1.5 is preferred. Although the mol ratio may be 1.0 or less, the yield of the target onium salt derivative having, as a counter ion to the onium moiety, a conjugated base of a sulfonic acid disadvantageously decreases. Although the mol ratio may be 1.5 or more, using a large excess amount of the sulfonic acid and/or a salt thereof is economically disadvantageous.

Although the reaction of the second step of the present invention may be carried out in the presence or absence of a solvent, the reaction is preferably carried out in the presence of a solvent. Examples of the solvent include water, halogenated hydrocarbons such as dichloromethane, chloroform, carbon tetrachloride, and chlorobenzene; ethers such as diethyl ether, diisopropyl ether, methyl t-butyl ether, and di-t-butyl ether; and nitriles such as acetonitrile and benzonitrile. Of these, water is preferred. A mixed solvent containing water and the above-described organic solvent is also preferred. No particular limitation is imposed on the reaction temperature of the second step.

BEST MODE FOR CARRYING OUT THE INVENTION

The present invention will next be described in more detail by way of examples, which should not be construed as limiting the invention thereto. Produced compounds were identified by NMR, IR, UV, and MASS.

EXAMPLE 1

Synthesis of bis(p-tert-butylphenyl)iodonium p-toluenesulfonate

Bis(p-tert-butylphenyl)iodonium chloride (428.8 g; 1.0 mol) and methyl p-toluenesulfonate (223.5 g; 1.2 mol) were suspended in t-butyl methyl ether (500 ml). The suspension was heated at 55° C.-58° C. and refluxed for 5 hours while being stirred. After the reaction mixture had been cooled, formed white solid was separated through filtration. The white solid was washed with t-butyl methyl ether and dried under vacuum, to thereby yield 513.7 g of bis(p-tert-butylphenyl)iodonium p-toluenesulfonate (yield: 91%).

The chloride anion content of the resultant white solid was 8 ppm, as determined by silver nitrate titration.

EXAMPLE 2

Synthesis of bis(p-tert-butylphenyl)iodonium p-toluenesulfonate

The procedure described in Example 1 was repeated, except that isopropyl p-toluenesulfonate (257.1 g; 1.2 mol) was used instead of methyl p-toluenesulfonate, to thereby yield 479.9 g of bis(p-tert-butylphenyl)iodonium p-toluenesulfonate (yield: 85%). The chloride anion content was determined to be 38 ppm.

EXAMPLE 3

Synthesis of Triphenylsulfonium p-toluenesulfonate

Acetonitrile (500 ml) was added to triphenylsulfonium iodide (390.3 g; 1.0 mol) and methyl p-toluenesulfonate (223.5 g; 1.2 mol). The resultant mixture was heated at 82° C.-85° C. and refluxed for 5 hours while being stirred. The reaction mixture was cooled, and acetonitrile was removed through distillation under reduced pressure. The thus-obtained pale-yellow solid was washed with methylene chloride, and dried under vacuum, to thereby yield 369.4 g of triphenylsulfonium p-toluenesulfonate (yield: 85%).

The iodide anion content of the resultant white solid matter was 83 ppm, as determined by silver nitrate titration.

EXAMPLE 4

Synthesis of bis(p-tert-butylphenyl)iodonium 9,10-dimethoxyanthracene-2-sulfonate Acetonitrile (90 ml) was added to bis(p-tert-butylphenyl)iodonium chloride (6.4 g; 15 mmol) and methyl 9,10-dimethoxyanthracene-2-sulfonate (6.48 g; 19.5 mmol). The resultant mixture was heated at 82° C.-85° C. and refluxed for 20 hours while being stirred. The reaction mixture was cooled, and precipitated solid was separated through filtration. The solid was washed with ethyl acetate, and dried under vacuum, to thereby yield 8.32 g of bis(p-tert-butylphenyl)iodonium 9,10-dimethoxyanthracene-2-sulfonate (yield: 78%). The chloride anion content of the resultant solid was 110 ppm, as determined by silver nitrate titration.

EXAMPLE 5

Synthesis of bis(p-tert-butylphenyl) Camphorsulfonate Iodonium

Ethyl acetate (50 ml) was added to bis(p-tert-butylphenyl)iodonium chloride (17.06 g; 39.79 mmol) and methyl camphorsulfonate (10.78 g; 43.76 mmol). The resultant mixture was heated at 77° C.-80° C. and refluxed for 24 hours while being stirred. The reaction mixture was cooled, and formed solid was removed through filteration. The solid was recrystallized from acetone, and dried under vacuum, to thereby yield 20.63 g of bis(p-tert-butylphenyl)iodonium camphorsulfonate (yield: 83%).

The chloride anion content of the resultant solid was 20 ppm, as determined by silver nitrate titration.

EXAMPLE 6

Synthesis of bis(p-tert-butylphenyl)iodonium p-toluenesulfonate

Bis(p-tert-butylphenyl)iodonium acetate (467 mg; 1.0 mmol) and methyl p-toluenesulfonate (204 mg; 1.1 mmol) were suspended in t-butyl methyl ether (5 ml). The suspension was heated at 55° C.-58° C. and refluxed for 5 hours while being stirred. The reaction mixture was cooled, and formed white solid was removed through filtration. The white solid was washed with t-butyl methyl ether, and dried under vacuum, to thereby yield 521 mg of bis(p-tert-butylphenyl)iodonium p-toluenesulfonate (yield: 91%).

EXAMPLE 7

Synthesis of bis(p-tert-butylphenyl)iodonium p-toluenesulfonate

The procedure described in Example 6 was repeated, except that isopropyl p-toluenesulfonate (257.1 mg; 1.2 mmol) was used instead of methyl p-toluenesulfonate, to

EXAMPLE 8

Synthesis of Triphenylsulfonium p-toluenesulfonate

Acetonitrile (5 ml) was added to triphenylsulfonium propionate (336 mg; 1.0 mmol) and methyl p-toluenesulfonate (204 mg; 1.1 mmol). The resultant mixture was refluxed for 5 hours while being stirred. The reaction mixture was cooled, and acetonitrile was removed through distillation under reduced pressure. The thus-obtained pale-yellow solid was washed with methylene chloride, and dried under vacuum, to thereby yield 492 mg of triphenylsulfonium p-toluenesulfonate (yield: 85%).

EXAMPLE 9

Synthesis of bis(p-tert-butylphenyl)iodonium Comphorsulfonate

Ethyl acetate (50 ml) was added to bis(p-tert-butylphenyl)iodonium acetate (467 mg; 1 mmol) and methyl camphorsulfonate (259 mg; 1.05 mmol). The resultant mixture was refluxed for 24 hours while being stirred. The reaction mixture was cooled, and formed solid was removed through filtration. The solid was recrystallized from acetone, and dried under vacuum, to thereby yield 518 mg of bis(p-tert-butylphenyl)iodonium camphorsulfonate (yield: 83%).

EXAMPLE 10

Synthesis of bis(p-tert-butylphenyl)iodonium trifluoromethanesulfonate tert-Butyl methyl ether (5 ml) was added to bis(p-tert-butylphenyl)iodonium acetate (467 mg; 1 mmol) and methyl trifluoromethanesulfonate (170 mg; 1.05 mmol), and the resultant mixture was allowed to react for 4 hours at room temperature while being stirred. The solid formed by reaction was purified and separated through filtration, and dried under vacuum, to thereby yield 412 mg of bis(p-tert-butylphenyl)iodonium trifluoromethanesulfonate (yield: 76%).

EXAMPLE 11

Production of Diphenyliodonium Trifluoromethanesulfonate

Diphenyliodonium chloride (1.67 kg) was added to acetonitrile (5.3 L) so as to form a slurry, and dimethylsulfuric acid (0.80 kg) was slowly added to the slurry while being stirred at room temperature. The reaction mixture was refluxed for one hour so as to allow the reaction to proceed, and acetonitrile serving as a reaction solvent was removed through distillation under reduced pressure. The thus-obtained white solid was dissolved in distilled water (12 L), and trifluoromethanesulfonic acid (0.95 kg) was slowly added dropwise to the solution, followed by stirring for 1 hour at ambient temperature. The mixture was separated through filtration, to thereby obtain white solid (2.4 kg). Since the thus-obtained solid contained a trace amount of acid, it was further recrystallized from distilled water (5 L). The thus-obtained crystals were removed through filtration and dried, to thereby yield 1.9 kg of diphenyliodonium trifluoromethanesulfonate as white solid (yield: 84%).

The resultant onium salt obtained in the above-described manner was analyzed by ion chromatography so as to determine the residual chloride anion content and the residual methylsulfate ion content. In each case, the corresponding ion content was confirmed to be not greater than 1 ppm.

EXAMPLE 12

Production of Triphenylsulfonium Trifluoromethanesulfonate

Triphenylsulfonium iodide (620 g) was added to acetonitrile (3 L) while being stirred at room temperature so as to form a slurry, and dimethylsulfuric acid (105 g) was slowly added to the slurry. After solid matter was completely dissolved, acetonitrile serving as a reaction solvent was removed through distillation under reduced pressure. The thus-obtained solid was dissolved in distilled water, and trifluoromethanesulfonic acid (288 g) was added dropwise to the resultant solution. The mixture was stirred for 1 hour, and the thus-obtained oily matter was taken up through extraction with dichloromethane. The resultant organic layer was washed with distilled water, and dichloromethane serving as a solvent was removed throuh distillation under reduced pressure, to thereby yield viscous oily matter. Ether was added to the oil phase, to thereby yield 440 g of triphenylsulfonium trifluoromethanesulfonate as white matter (yield: 67%).

The onium salt obtained in the above-described manner was analyzed by ion chromatography so as to determine the residual iodide anion content and the residual methylsulfate ion content. In each case, the corresponding ion content was confirmed to be not greater than 1 ppm.

EXAMPLE 13

Production of Triphenylsulfonium Nonaflate

Triphenylsulfonium iodide (270 g) was added to acetonitrile (2.1 L) while being stirred at room temperature so as to form a slurry, and dimethylsulfuric acid (105 g) was slowly added to the slurry. After the solid was completely dissolved, acetonitrile serving as a reaction solvent was removed through distillation under reduced pressure. Potassium nonaflate (274 g) was added to the thus-obtained solid, and the resultant mixture was dissolved in distilled water (2 L). This mixture was stirred for 1 hour, and the thus-obtained oily matter was taken up through extraction with dichloromethane. The formed organic layer was washed with distilled water, and dichloromethane serving as a solvent was removed through distillation under reduced pressure, to thereby yield viscous oily matter. Ether was added to the oil phase, to thereby yield 425 g of triphenylsulfonium nonaflate as white matter (yield: 83%).

The onium salt obtained in the above-described manner was analyzed by ion chromatography so as to determine the residual iodide anion content and the residual methylsulfate ion content. In each case, the corresponding ion content was confirmed to be not greater than 1 ppm.

EXAMPLE 14

Production of Triphenylsulfonium Camphorsulfonate

Triphenylsulfonium iodide (40 g) was added to acetonitrile (200 ml) while being stirred at room temperature so as to form a slurry, and dimethylsulfuric acid (15 g) was slowly added to the slurry. After solid was completely dissolved, camphorsulfonic acid (49 g) was added to the mixture, followed by stirring for 12 hours. Acetonitrile serving as a solvent was removed through distillation under reduced pressure, to thereby yield oily matter. The oily matter was dissolved in dichloromethane, and the organic layer was washed with distilled water. Dichloromethane serving as a solvent was removed through distillation under reduced pressure, to thereby yield viscous oily matter. Ether was added to the oil phase, to thereby yield 9 g of triphenylsulfonium camphorsulfonate as white matter (yield: 18%).

The onium salt obtained in the above-described manner was analyzed by ion chromatography so as to determine the residual iodide anion content and the residual methylsulfate ion content. In each case, the corresponding ion content was confirmed to be not greater than 1 ppm.

EXAMPLE 15

Production of Triphenylsulfonium Methylsulfate

Triphenylsulfonium iodide (3.9 g) was added to acetonitrile (10 ml) while being stirred at room temperature so as to form a slurry, and dimethylsulfuric acid (1.5 g) was slowly added to the slurry. After solid was completely dissolved, acetonitrile serving as a solvent was evaporated under reduced pressure. Ether was slowly added to the thus-obtained viscous solid, to thereby yield 3.2 g of white precipitates (yield: 85%).

The white precipitates were analyzed by 1H-NMR and C13-NMR, and were confirmed to be triphenylsulfonium methylsulfate.

EXAMPLE 16

Synthesis of Diphenyliodonium Tosylate—(1)

Diphenyliodonium chloride (315 mg; 1 mmol), ethyl orthoformate (296 mg; 2 mmol), and anhydrous toluenesulfonic acid (207 mg; 1.2 mmol) were dissolved in anhydrous methylene chloride (5 ml), and the resultant mixture was refluxed for 5 hours while being stirred. The reaction mixture was alkalinized by adding 1% aqueous ammonia (10 ml), and subjected to extraction with methylene chloride twice, followed by drying. The solvent was removed through distillation, and the thus-obtained solid matter was washed with ether, to thereby yield 229 mg of the target compound as white crystals (yield: 75%).

The anion content of the resultant compound was determined by ion chromatography. The chloride anion content was determined to be not greater than 50 ppm.

EXAMPLE 17

Synthesis of Diphenyliodonium Tosylate—(2)

Diphenyliodonium chloride (315 mg; 1 mmol), methyl orthocarbonate (2 mg; 2 mmol), and anhydrous toluenesulfonic acid (207 mg; 1.2 mmol) were dissolved in anhydrous methylene chloride (5 ml), and the resultant mixture was stirred for 2 hours at room temperature. The reaction mixture was alkalinized by adding 1% aqueous ammonia (10 ml), and subjected to extraction with methylene chloride twice, followed by drying. The solvent was removed through distillation, and the thus-obtained solid matter was washed with ether, to thereby yield 280 mg of the target compound as white crystals (yield: 92%).

The anion content of the resultant compound was determined by ion chromatography. The chloride anion content was determined to be not greater than 14 ppm.

EXAMPLE 18

Synthesis of Triphenylsulfonium Camphorsulfonate

Triphenylsulfonium iodide (390 mg; 1 mmol), ethyl orthoacetate (486 mg; 3 mmol), and camphorsulfonic acid (278 mg; 1.2 mmol) were dissolved in anhydrous methylene chloride (10 ml), and the resultant mixture was stirred for 12 hours at room temperature. The reaction mixture was alkalinized by adding 1% aqueous ammonia (10 ml), and subjected to extraction with methylene chloride three times, followed by drying. The solvent was removed through distillation, and the thus-obtained semi-solid matter was washed with ether, to thereby yield 410 mg of the target compound as white crystals (yield: 82%).

The anion content of the resultant compound was determined by ion chromatography. The chloride anion content was determined to be not greater than 10 ppm.

EXAMPLE 19

Synthesis of di-tert-butylphenyliodonium Triflate

Di-tert-butylphenyliodonium chloride (443 mg; 1 mmol), ethyl orthopropionate (211 mg; 1.5 mmol), and trifluoromethanesulfonic acid (165 mg; 1.1 mmol) were dissolved in anhydrous methylene chloride (10 ml), and the resultant mixture was stirred for 2 hours at room temperature. The reaction mixture was alkalinized by adding 1% aqueous ammonia (10 ml), and extracted with methylene chloride twice, followed by drying. The solvent was evaporated, and the thus-obtained solid matter was washed with ether, to thereby yield 491 mg of the target compound as white crystals (yield: 91%).

The anion content of the resultant compound was determined by ion chromatography. The chloride anion content was determined to be not greater than 10 ppm.

EXAMPLE 20

Synthesis of di-tert-butylphenyliodonium Pentafluorobenzenesulfonate

Di-tert-butylphenyliodonium chloride (443 mg; 1 mmol), ethyl orthoacetate (342 mg; 2 mmol), and pentafluorobenzenesulfonic acid (298 mg; 1.2 mmol) were dissolved in chloroform (5 ml), and the resultant mixture was refluxed for 2 hours while being stirred. The solvent was removed through distillation, and the thus-obtained solid matter was washed with ether, to thereby yield 436 mg of the target compound as white crystals (yield: 68%).

The anion content of the resultant compound was determined by ion chromatography. The chloride anion content was determined to be not greater than 5 ppm.

EXAMPLE 21

Synthesis of Triphenylsulfonium 4-trifluoromethylbenzenesulfonate

Triphenylsulfonium bromide (343 mg; 1 mmol), ethyl orthoformate (296 mg; 2 mmol), and 4-trifluoromethylbenzenesulfonic acid (271 mg; 1.2 mmol) were dissolved in methylene chloride (10 ml), and the mixture was stirred for 6 hours at room temperature. The reaction mixture was alkalinized by adding 1% aqueous ammonia (10 ml), and subjected to extraction with methylene chloride three times, followed by drying. The solvent was removed through distillation, to thereby yield solid matter. The solid matter was washed and stirred in ether, to thereby yield 375 mg of the target compound as white crystals (yield: 76%).

The anion content of the resultant compound was determined by ion chromatography. The chloride anion content was determined to be not greater than 5 ppm.

EXAMPLE 22

Synthesis of Diphenyliodonium Triflate

Diphenyliodonium dimethylphosphate (315 mg; 1 mmol) and trifluoromethanesulfonic acid (158 mg; 1.01 mmol) were dissolved in methylene chloride (10 ml), and the resultant mixture was stirred. Half volume of the solvent was removed from the methylene chloride solution through distillation, and ether (50 ml) was added thereto. The mixture was stirred, to thereby precipitate 109 mg of the target compound as white crystals (yield: 72%).

EXAMPLE 23

Synthesis of Triphenylsulfonium Toluenesulfonate

Diphenyliodonium dimethylphosphate (315 mg; 1 mmol) and p-toluenesulfonic acid (189 mg; 1.1 mmol) were dissolved in methylene chloride (10 ml), and the mixture was stirred, followed by addition of 1% aqueous ammonia (10 ml). After the alkalinity of the solution was confirmed, the solution was stirred vigorously. The thus-obtained mixture was allowed to stand, and the aqueous layer was separated. The aqueous layer was washed with water successively until the aqueous layer exhibited neutral pH. The methylene chloride solution was dried, and the solvent was removed through distillation. The residue was washed in ether by stirring, to thereby precipitate 214 mg of the target compound as white crystals (yield: 84%).

EXAMPLE 24

Synthesis of Diphenyliodonium Camphorsulfonate

Diphenyliodonium dimethylphosphate (315 mg; 1 mmol) and camphorsulfonic acid (254 mg; 1.1 mmol) were dissolved in methylene chloride (10 ml), and the resultant mixture was stirred, followed by addition of 1% aqueous ammonia (10 ml). After the alkalinity of the solution was confirmed, the solution was stirred vigorously. The thus-obtained mixture was allowed to stand, and the aqueous layer was separated. The aqueous layer was washed with water successively until the aqueous layer exhibited neutral pH. The methylene chloride solution was dried, and the solvent was removed through distillation. The residue was washed in ether by stirring, to thereby precipitate 465 mg of the target compound as white crystals (yield: 91%).

EXAMPLE 25

Synthesis of di-tert-butylphenyliodonium Perfluorobenzenesulfonate

Di-tert-butylphenyliodonium diethylphosphate (546 mg; 1 mmol) and perfluorobenzenesulfonic acid (267 mg; 1.1 mmol) were dissolved in methylene chloride (10 ml), and 1% aqueous ammonia (10 ml) was added thereto. After the alkalinity of the solution was confirmed, the solution was stirred vigorously. The thus-obtained mixture was allowed to stand, and the aqueous layer was separated. The aqueous layer was washed with water successively until the aqueous layer exhibited neutral pH. The methylene chloride solution was dried, and the solvent was removed through distillation. The residue was washed in ether by stirring, to thereby precipitate 435 mg of the target compound as white crystals (yield: 68%).

EXAMPLE 26

Synthesis of di-tert-butylphenyliodonium Perfluorobutanesulfonate

Di-tert-butylphenyliodonium diethylphosphate (546 mg; 1 mmol) and sodium perfluorobutanesulfonate (354 mg; 1.1 mmol) were dissolved in water (10 ml), and the resultant mixture was extracted three times with methylene chloride (10 ml). The solvent was removed through distillation, and precipitated white solid was washed with ether, followed by recrystallization from a mixture of methylene chloride and ether, to thereby precipitate 561 mg of the target compound as white crystals (yield: 81%).

EXAMPLE 27

Synthesis of Diphenyliodonium Dimethylphosphonate

Diphenyliodonium chloride (315 mg; 1 mmol) and trimethyl phosphate (1 g) were stirred at 170° C. for 10 minutes. After the reactants were dissolved, the mixture was cooled, to thereby yield solid matter. The solid matter was washed with ether, to thereby yield 250 mg of the target compound as white crystals (yield: 81.6%). The anion content of the resultant compound was determined by ion chromatography. The chloride anion content was determined to be not greater than 10 ppm.

EXAMPLE 28

Synthesis of Triphenylsulfonium Dimethylphosphonate

A mixture of triphenylsulfonium iodide (390 mg; 1 mmol) and trimethyl phosphate (1 g) was stirred at 130° C. for 3 hours. Subsequently, the homogenous solution was cooled, and the thus-obtained solid matter was washed with IPA, to thereby yield 280 mg of the target compound as white crystals (yield: 72.2%). The anion content of the resultant compound was determined by ion chromatography. The iodide anion content was determined to be not greater than 50 ppm.

EXAMPLE 29

Synthesis of di-tert-butylphenyliodonium Dimethylphosphate—(1)

A solution containing di-tert-butylphenyliodonium chloride (443 mg; 1 mmol) and trimethyl phosphate (2 g) was stirred at 110° C. for 1 hour. The thus-obtained solid matter was washed with ether, to thereby yield 420 mg of the target compound as white crystals (yield: 78.7%) (iodonium chloride (starting compound) can be removed by washing with acetone.).

EXAMPLE 30

Synthesis of di-tert-butylphenyliodonium Dimethylphosphate—(2)

Di-tert-butylphenyliodonium chloride (443 mg; 1 mmol) and trimethyl phosphate (0.5 g) were dissolved in chloroform (5 ml), and the mixture was refluxed for 12 hours while being stirred. The solvent was removed through distillation, and the thus-obtained solid matter was washed with ether, to thereby yield 400 mg of the target compound as white crystals (yield: 75.2%)

EXAMPLE 31

Synthesis of di-tert-butylphenyliodonium Diethylphosphate

A solution containing di-tert-butylphenyliodonium chloride (443 mg; 1 mmol) and triethyl phosphate (3 g) was stirred at 110-120° C. for 1 hour. The thus-obtained solid matter was washed with ether, to thereby yield 432 mg of the target compound as white crystals (yield: 69.2%).

EXAMPLE 32

The following is an example of the method for preparing an onium salt derivative having, as a counter ion to the onium moiety, a conjugated base of sulfonic acid by use of di-tert-butylphenyliodonium dimethylphosphate as starting material.

Di-tert-butylphenyliodonium dimethylphosphate (533 mg; 1 mmol) and p-toluenesulfonic acid (140 mg; 1.1 mmol) were dissolved in methylene chloride (10 ml). The solution was alkalinized by adding 1% aqueous ammonia (10 ml), and the mixture was stirred for 10 minutes. The methylene chloride layer was taken up through extraction, and washed with water, followed by drying. The solvent was removed through distillation, and the thus-obtained crude crystals were recrystallized from ether/methylene chloride, to thereby yield 410 mg of the target compound, di-tert-butylphenyliodonium dimethylsulfonate, as white crystals (yield: 77.2%).

As described herinabove, the present invention provides high-yield methods for producing onium salt derivatives useful as agents such as acid generators employed in chemically amplified resists; as well as novel onium salt derivatives.

The invention claimed is:

1. A method for producing an onium salt derivative, characterized by comprising reacting an onium salt which has a halide Q as an anion moiety and which is represented by any one of formulas (3) or (4):

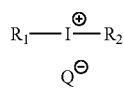

(1)

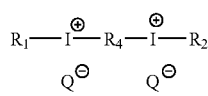

(2)

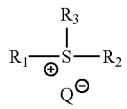

(3)

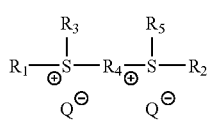

(4)

wherein each of $R_1$, $R_2$, $R_3$, and $R_5$ represents an alkyl group, a cycloalkyl group, a perfluoroalkyl group, an aromatic organic group, an aralkyl group, or a phenacyl group, each of these groups having $\leq 25$ carbon atoms and being optionally substituted; one or both of the pairs of $R_1$ and $R_3$, and $R_2$ and $R_5$ may together form a divalent organic group; $R_4$ represents a $C \leq 20$ divalent organic group; and Q represents a halide anion, with an ester compound which has an alkyl group $R_7$ and which is represented by formula (5):

(5)

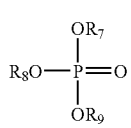

(6)

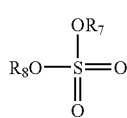

(7)

wherein $R_6$ represents an alkyl group, a cycloalkyl group, a perfluoroalkyl group, an aromatic organic group, or an aralkyl group, each of these groups having $\leq 25$ carbon atoms and being optionally substituted; $R_7$ represents an alkyl group, having $\leq 5$ carbon atoms and being optionally substituted;

to thereby form $R_7Q$ through nucleophilic attack by the halide Q on the alkyl group R7 of the ester compound, and to also produce an onium salt derivative which is formed of an anion represented by $R_6SO_2O$—, derived from the ester compound and an onium cation derived from the onium salt, an onium salt derivative represented by formulas (10) or (11)

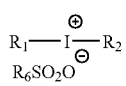

(8)

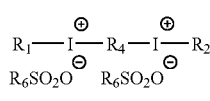

(9)

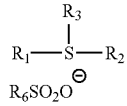

(10)

-continued
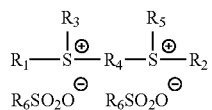 (10)
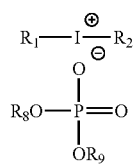 (11)
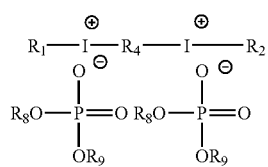 (12)
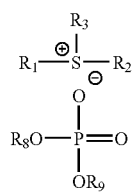 (13)
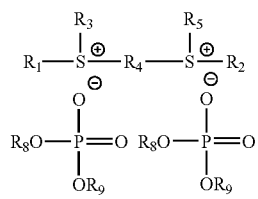 (14)
-continued
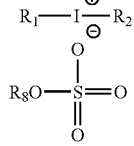 (15)
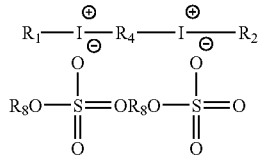 (16)
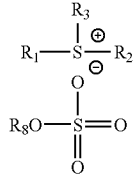 (17)
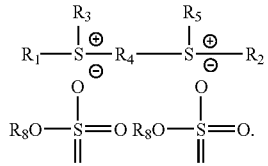 (18)
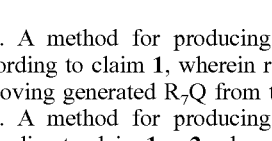 (19)
2. A method for producing an onium salt derivative according to claim 1, wherein reaction is carried out while removing generated $R_7Q$ from the reaction system.
3. A method for producing an onium salt derivative according to claim 1 or 2, wherein the reaction is carried out in a solvent.
* * * * *